(12) United States Patent
Williams et al.

(10) Patent No.: US 8,053,004 B2
(45) Date of Patent: Nov. 8, 2011

(54) OINTMENT FOR TOPICAL TREATMENT OF HOT FLASHES AND METHOD OF USE

(75) Inventors: Anson Williams, Malibu, CA (US); Joanna Connell, Newbury Park, CA (US)

(73) Assignee: Starmaker Products, LLC, Newbury Park, CA (US)

( * ) Notice: Subject to any disclaimer, the term of this patent is extended or adjusted under 35 U.S.C. 154(b) by 0 days.

(21) Appl. No.: 12/080,346

(22) Filed: Apr. 1, 2008

(65) Prior Publication Data

US 2009/0092688 A1 Apr. 9, 2009

Related U.S. Application Data

(60) Provisional application No. 60/978,337, filed on Oct. 8, 2007.

(51) Int. Cl.
  *A61K 36/53* (2006.01)
  *A61K 36/25* (2006.01)
  *A61K 36/16* (2006.01)
  *A61K 36/00* (2006.01)

(52) U.S. Cl. ......... 424/747; 424/728; 424/752; 424/725

(58) Field of Classification Search .................. None
See application file for complete search history.

(56) References Cited

U.S. PATENT DOCUMENTS

| | | | |
|---|---|---|---|
| 4,096,254 A | 6/1978 | Benson et al. | |
| 5,658,578 A * | 8/1997 | Ogawa et al. | 424/401 |
| 5,874,084 A | 2/1999 | Yng-Wong | |
| 5,962,505 A | 10/1999 | Bobrove et al. | |
| 6,395,757 B1 | 5/2002 | Bobrove et al. | |
| 6,433,003 B1 | 8/2002 | Bobrove et al. | |
| 6,503,517 B1 * | 1/2003 | Mohammadi et al. | 424/401 |
| 6,518,319 B1 | 2/2003 | Empie et al. | |
| 6,586,018 B1 | 7/2003 | Fasano | |
| 6,899,901 B2 | 5/2005 | Nakatsu et al. | |
| 7,179,494 B1 | 2/2007 | Marchese et al. | |
| 7,375,203 B2 * | 5/2008 | Flores et al. | 536/23.1 |
| 2002/0086039 A1 * | 7/2002 | Lee et al. | 424/401 |
| 2003/0138394 A1 * | 7/2003 | Charrouf et al. | 424/74 |
| 2003/0170325 A1 | 9/2003 | Mermelstein et al. | |
| 2005/0142080 A1 * | 6/2005 | Goppel et al. | 424/59 |
| 2005/0255070 A1 * | 11/2005 | Albano | 424/70.14 |
| 2007/0122460 A1 * | 5/2007 | Daily | 424/443 |
| 2007/0224138 A1 * | 9/2007 | Gibbons | 424/60 |
| 2007/0243220 A1 * | 10/2007 | Sandewicz et al. | 424/401 |
| 2007/0275021 A1 * | 11/2007 | Lee et al. | 424/401 |
| 2007/0281998 A1 | 12/2007 | LaGuardia | |
| 2007/0286831 A1 * | 12/2007 | Kamada et al. | 424/70.7 |
| 2008/0025920 A1 | 1/2008 | Simes et al. | |
| 2008/0033376 A1 | 2/2008 | Cammarata | |
| 2008/0038300 A1 * | 2/2008 | Jaspers et al. | 424/401 |
| 2008/0181974 A1 * | 7/2008 | Cauchard et al. | 424/725 |
| 2008/0206273 A1 * | 8/2008 | Ambrosen et al. | 424/195.17 |
| 2008/0241200 A1 * | 10/2008 | Sojka | 424/401 |
| 2008/0275138 A1 * | 11/2008 | Ridley et al. | 514/772.6 |
| 2009/0275669 A1 * | 11/2009 | Aida et al. | 514/772 |

FOREIGN PATENT DOCUMENTS

| | | |
|---|---|---|
| CN | 1146344 A * | 4/1997 |
| CN | 95113012 | 4/1997 |
| FR | 2898059 | 9/2007 |
| WO | WO 0012087 | 3/2000 |
| WO | WO 2007081293 | 7/2007 |

OTHER PUBLICATIONS

R. Eccles, Menthol and Related Cooling Compounds, Journal of Pharmacy and Pharmacology, 46, pp. 618-630 (1994).

* cited by examiner

*Primary Examiner* — Christopher R Tate
*Assistant Examiner* — Randall Winston
(74) *Attorney, Agent, or Firm* — Christopher R. Balzan

(57) ABSTRACT

A composition and method of use therefore that provides for the objective topical treatment of hot flashes that is clinically shown to objectively reduce skin temperature, with the effective ingredients including menthol and peppermint oil which can be substituted with spearmint oil. The method involves application of the composition, which can be in the form of a liquid, crème, topical gel, mist or moist towelette and which is applied most optimally to the back of the neck, the front of the neck, behind the ears and on the wrists of the sufferer.

22 Claims, No Drawings

OINTMENT FOR TOPICAL TREATMENT OF HOT FLASHES AND METHOD OF USE

REFERENCE TO PRIOR APPLICATION

This application claims the priority of provisional application 60/978,337, filed Oct. 8, 2007 entitled A NON-PRESCRIPTION LIQUID, CRÈME, OR MOIST TOILETTE THAT, AFTER APPLIED AND RUBBED BY HAND INTO HUMAN SKIN, IS CLINICALLY PROVEN TO REDUCE SKIN TEMPERATURE by Anson Williams and inadvertently omitted co-inventor Joanna Connell.

BACKGROUND OF THE INVENTION

1. Field of the Invention

The present invention relates generally to the field of the treatment of hot flashes and particularly to a composition clinically proven to reduce skin temperature and a method of use thereof.

2. Description of the Prior Art

Upon reaching menopause, many women experience what are known as hot flashes. The most common remedy to curb such flashes is the administration of hormones, such as estrogen, with known harmful side effects. A hot flash is characterized by a sudden, intense, hot feeling on the face and upper body. Often the hot flash can be preceded or accompanied by a rapid heartbeat and sweating, nausea, dizziness, anxiety, headache, weakness, or a feeling of suffocation. Some women experience a general, overall uneasy feeling just before the hot flash.

A hot flash is generally followed by a flush, leaving the sufferer reddened and perspiring. High intensity hot flashes can result in the sufferer becoming soaked in perspiration. Lower intensity flashes cause merely produce a moist upper lip. A chill often precedes the flash, but can also occur at the conclusion of the flash. When hot flashes occur during the night, they sufferer can't sleep, resulting in poor concentration, memory problems, irritability and exhaustion during the day.

The exact cause of hot flashes is not currently known. Some theories suggest that hot flashes are due to a drop in the body's level of female hormones called estrogens, usually related to menopause. This drop in turn affects the hypothalamus, an area of the brain that regulates body temperature. During a hot flash, the hypothalamus appears to believe that the body is too hot even when it is not, and tells the body to release the excess heat. As a result, the heart pumps faster and the blood vessels in the skin dilate. Areas of skin dilation are particularly noticeable in those areas near the skin of the head, face, neck and chest. This skin dilation cause more blood to circulate in order to radiate off the heat. The sweat glands then release sweat to cool the body off even more. Once the blood vessels return to normal size, the sufferer feels cool again.

This natural heat-releasing mechanism is how the body keeps from overheating during high temperatures. However, when a drop in estrogen triggers the process instead, often due to menopause, the brain's confused response can make a person very uncomfortable. Raises in skin temperature have been found as high as 6° C. during an episode. As a result of the brain's confusion, the body cools down when it shouldn't, and the sufferer is miserable, often becoming soaking wet in the middle of a board meeting or in the middle of the night.

Around 85% of women suffer hot flashes during the years immediately before and after menopause, which occurs on average around the age of 51. Hot flashes can begin as early as 2 to 3 years prior to the last menstrual period, however. The hot flashes can last up to six months or go as long as after 15 years after the last menstrual period. On average, the hot flashes continue for two years. The frequency of episodes varies widely, from a few episodes a year to up to 20 episodes a day.

Although hot flashes usually are considered a female problem, men can have hot flashes if their levels of the male sex hormone testosterone drop suddenly and dramatically. For example, hot flashes occur in 75% of men with prostate cancer who have surgery to remove the testes or who take medication to decrease testosterone levels.

Symptoms that mimic hot flashes can occur in both men and women who have a tumor of the hypothalamus or pituitary gland, as well as with those who have suffered from certain serious infections, such as tuberculosis or HIV, those with alcoholism or those who suffer from thyroid disorders. Symptoms that are similar to hot flashes also can be a side effect of the food additive monosodium glutamate (MSG), or of certain medications, particularly nitroglycerin, nifedipine, niacin, vancomycin and calcitonin.

Most commonly, Hormone Replacement Therapy is believed to be one of the most effective treatments available to reduce the onset of hot flashes. These hormones can be taken orally, intravenously, transdermally and/or topically, applied in a cream. Alternative medications to help decrease the intensity of hot flashes include clonidine, lofexidine, methyldopa, or antidepressants such as venlafaxine, paroxetine, fluoxetine and sertraline.

In addition to Hormone Replacement Therapy and the other medications noted above, several nonprescription dietary supplements or herbal remedies have been promoted as natural ways to prevent or treat hot flashes. Several studies in humans suggest that black cohosh, red clover and soy may be safe and effective for improving symptoms of menopause. There are several other known suggested hot flash remedies such as changing one's wardrobe, becoming physically active, reducing intake of triggering foods and beverages and relaxation that are aimed at preventing or reducing the number of hot flashes experienced.

Certain drawbacks exist with current treatments for hot flashes. Because of potential side effects and dangers of hormone therapy, as outlined in several medical studies, many women choose not to use Hormone Replacement Therapy in any form. Also, because other medications or dietary supplements are often ineffective or can cause undesired effects, many women choose to forgo these treatments as well.

Even when effective, however, the above-mentioned remedies are geared at reducing the onset of a hot flash rather than treating the symptoms or relieving the discomfort of an ongoing hot flash. Therefore, when a hot flash occurs, these treatments do little if anything to reduce the intense hot feeling on the face and upper body, rapid heartbeat, sweating, nausea, dizziness, anxiety, headache, weakness or a feeling of suffocation after they have occurred.

Topical treatments for counteracting menopause symptoms have been the subject of earlier patent documents. One example is U.S. Patent Publication No. 2008/0033376 to Cammarata, which discloses a composition that comprises an alcohol and an aloe vera gel for topically treating hot flashes and methods for the storing, dispensing and application thereof. This composition is applied to the body to effectively cool the skin temperature, but the composition does not include the components found in the instant invention. More importantly, however, is that the Cammarata method and composition only effectively cools the subject, giving the sense of cooling, whereas the composition and method of the instant invention has been clinically proven to actually lower skin temperature. The user is not tricked into feeling cooler with this composition, but actually is objectively cooler.

Also of note is U.S. Patent Publication No. 2003/0170325, which teaches a composition for primarily for the treatment of vaginal dryness, only mentions other symptoms of menopause in passing and is not specifically meant to reduce skin temperature in the treatment of hot flashes.

In addition, U.S. Pat. No. 5,962,505 describes a method for alleviating hot flashes comprising the step of a therapeutically effective amount of a glycopyrrolate compound such that the hot flashes are substantially reduced, wherein the glycopyrrolate compound is applied to the skin. Glycopyrrolate, however, has its own side effects, such as reducing the body's sweating ability, causing fever and heat stroke in high temperatures, which is antithetical to the aim of the instant invention. Further side effects include dry mouth, difficulty urinating, headaches, diarrhea and constipation. The medication can also induce drowsiness or blurred vision, an effect exacerbated by the consumption of alcohol. Accordingly, the instant invention is an improvement over this remedy as it does not contain this medication nor does it risk any of the side effects associated with it.

There is therefore a need for a topical remedy that is clinically proven to bring down skin temperature in defined areas to relieve hot flashes. The instant invention discloses a remedy that is made from natural products which has a minimal to no detrimental side effects to the user.

SUMMARY OF THE INVENTION

The preferred embodiment of the present invention teaches a composition for the treatment of hot flashes that objectively lowers the skin temperature of the user comprising menthol.

The above embodiment can be further modified by defining that the composition further comprises peppermint oil.

The above embodiment can be further modified by defining that spearmint oil can be used in the place of peppermint oil.

The above embodiment can be modified by defining that the composition further includes butylene glycol.

The above embodiment can be further modified by defining that the composition further includes dimethicone, trisiloxane, Ceteth-10 and Laureth-4.

The above embodiment can be further modified by defining that the composition further includes sodium polyacrylate, hydrogenated polydecene and Trideceth-10.

The above embodiment can be further modified by defining that the composition further includes propylene glycol, diazolidinyl urea, methylparaben and propylparaben.

The above embodiment can be further modified by defining that the composition further includes ethoxydiglycol.

The above embodiment can be further modified by defining that the composition further includes Ginseng Extract.

The above embodiment can be further modified by defining that the composition further includes Arnica extract.

The above embodiment can be further modified by defining that the composition further includes Gingko Biloba extract.

A second embodiment of the instant invention teaches a method for the treatment of hot flashes that objectively lowers the skin temperature of the user comprising the steps of obtaining the composition that objectively lowers skin temperature, the composition further comprising menthol; and applying the composition to human skin at the beginning of a feeling of rising skin temperature due to a hot flash or hot weather conditions.

The above embodiment can be further modified by defining that the composition further comprises peppermint oil.

The above embodiment can be further modified by defining that spearmint oil can be used in place of peppermint oil.

The above embodiment can be further modified by defining that the composition is hydrolyzed and applied as a spray-on mist.

The above embodiment can be further modified by defining that the composition is applied as an ointment by rubbing into the skin.

The above embodiment can be further modified by defining that the ointment is a topical gel.

The above embodiment can be further modified by defining that the ointment is a crème.

The above embodiment can be further modified by defining that the composition is applied using a towelette.

The above embodiment can be further modified by defining that the composition is applied to the back of the neck.

The above embodiment can be further modified by defining that the composition is applied to the front of the neck.

The above embodiment can be further modified by defining that the composition is applied behind the ear.

The above embodiment can be further modified by defining that the composition is applied to the wrists.

DETAILED DESCRIPTION OF A PREFERRED EMBODIMENT

The instant invention involves a composition that results in a product that a person suffering from hot flashes can apply to back of the neck, behind the ears, the wrists, the bottom of the neck/top of the chest and the back of the neck for the immediate relief from the discomfort causes by the hot flashes, by objectively reducing the skin temperature of the sufferer. The composition was studied clinically to evaluate its effectiveness to reduce skin surface temperature during episodes of hot flashes in menopausal and post-menopausal women.

Under the study conditions, 27 healthy women between the ages of 45-65 years of age completed a one week clinical study. Results discussed include data from skin surface temperate and subject scores of severity of hot flashes.

The data analysis of skin surface temperature found that 100% of the subjects (27/27) showed a decrease in skin surface temperature on the treated test sites. A mean decrease in skin surface temperature by 1.57° C./2.8° F. was seen on the treated test sites. Up to a 3° C./5.4° F. decrease was seen in skin surface temperature in an individual subject on the treated test sites. A statistically significant decrease was found in skin surface temperature on the treated test sites.

The data analysis of subject scores showed that 100% of subjects reported experiencing relief from hot flashes after test product use. The mean scores for hot flashes before treatment with the test product on each day ranges from 1.95 to 2.34 (moderate to severe). The mean scores for hot flashes after treatment with the test product on each day range from 1.19 to 1.40 (mild to moderate). A statistically significant decrease in the severity of hot flashes as scored by the subjects was found on use of the test product for a period of one week.

Overall, the product proved to cool and decrease skin surface temperature providing relief from hot flashes and to decrease the severity of hot flashes.

The composition of the ointment in its preferred embodiment is as follows:

| | |
|---|---|
| Water | 30-100% |
| Butylene Glycol | 3-<10% |

-continued

| | |
|---|---|
| Dimethicone and trisiloxane and Ceteth-10 and Laureth-4 | 1-<3% |
| Sodium Polyacrylate and Hydrogenated Polydecene and Trideceth-10 | 1-<3% |
| Propylene glycol and Diazolidinyl Urea and Methylparaben and Propylparaben | 1-<3% |
| Ethoxydiglycol | 1-<3% |
| Menthol | 0.1-<1% |
| Peppermint Oil | 0.1-<1% |
| Ginseng Extract | <0.1% |
| *Arnica* Extract | <0.1% |
| Ginkogo Biloba Extract | <0.1% |

The composition can be modified by replacing peppermint oil with spearmint oil. The effective ingredients include menthol and peppermint oil which can be substituted with spearmint oil.

The Method is as follows: The composition is applied to human skin at the beginning of a hot flash or hot weather conditions to lower skin temperature causing relief of symptoms. The composition can be hydrolyzed and then misted or sprayed onto human skin instead or rubbing into skin. The ointment is typically applied by rubbing it into the skin as a topical gel, a crème, a mist, a liquid or in a wet toweled form. Locations on the skin for application for best results include the back of the neck, the front of the neck, behind the ears and on the wrists.

The illustrations and examples provided herein are for explanatory purposes and are not intended to limit the scope of the appended claims. This disclosure is to be considered an exemplification of the principles of the invention and is not intended to limit the spirit and scope of the invention and/or claims of the embodiment illustrated. Those skilled in the art will make modifications to the invention for particular applications of the invention.

The discussion included in this patent is intended to serve as a basic description. The reader should be aware that the specific discussion may not explicitly describe all embodiments possible and alternatives are implicit. Also, this discussion may not fully explain the generic nature of the invention and may not explicitly show how each feature or element can actually be representative or equivalent elements. Again, these are implicitly included in this disclosure. Where the invention is described in device-oriented terminology, each element of the device implicitly performs a function. It should also be understood that a variety of changes may be made without departing from the essence of the invention. Such changes are also implicitly included in the description. These changes still fall within the scope of this invention.

Further, each of the various elements of the invention and claims may also be achieved in a variety of manners. This disclosure should be understood to encompass each such variation, be it a variation of any apparatus embodiment, a method embodiment, or even merely a variation of any element of these. Particularly, it should be understood that as the disclosure relates to elements of the invention, the words for each element may be expressed by equivalent apparatus terms even if only the function or result is the same. Such equivalent, broader, or even more generic terms should be considered to be encompassed in the description of each element or action. Such terms can be substituted where desired to make explicit the implicitly broad coverage to which this invention is entitled. It should be understood that all actions may be expressed as a means for taking that action or as an element which causes that action. Similarly, each physical element disclosed should be understood to encompass a disclosure of the action which that physical element facilitates. Such changes and alternative terms are to be understood to be explicitly included in the description.

What is claimed is:

1. A composition for treating hot flashes comprising:
    a) an ingredient effective to objectively lower skin temperature, the effective ingredient comprising menthol, the effective ingredient being combined with inactive ingredients forming a topical ointment effective to actually objectively lower skin temperature when applied to the skin;
    b) wherein the composition further comprises about 0.1 to less than about 1 percent of at least one of: (1) peppermint oil; or (2) spearmint oil;
    c) wherein the composition comprises the menthol in an amount of about 0.1 to less than about 1 percent in addition to any menthol present in the at least one of peppermint oil or spearmint oil; and
    d) one or more extracts of: (1) ginsing; (2) arnica; or (3) gingko biloba.

2. The composition for treating hot flashes of claim 1, wherein the composition includes the peppermint oil.

3. The composition for treating hot flashes of claim 1, wherein the composition includes the spearmint oil.

4. The composition for treating hot flashes of claim 1, wherein the composition further includes butylene glycol.

5. The composition for treating hot flashes of claim 1, wherein the composition further includes at least one of: (a) dimethicone; (b) trisiloxane; (c) Ceteth-10; or (d) Laureth-4.

6. The composition for treating hot flashes of claim 1, wherein the composition further includes at least one of: (a) sodium polyacrylate; (b) hydrogenated polydecene; or (c) Trideceth.

7. The composition for treating hot flashes of claim 1, wherein the composition further includes at least one of: (a) propylene glycol; (b) diazolidinyl urea; (c) methylparaben; or (d) propylparaben.

8. The composition for treating hot flashes of claim 1, wherein the composition further includes ethoxydiglycol.

9. The composition for treating hot flashes of claim 1, wherein the composition includes ginseng extract.

10. The composition for treating hot flashes of claim 1, wherein the composition includes arnica extract.

11. The composition for treating hot flashes of claim 1, wherein the composition includes gingko biloba extract.

12. The composition for treating hot flashes of claim 1, wherein the composition further comprises:
    (a) butylene glycol; (b) dimethicone, trisiloxane, Ceteth-10, and Laureth-4; (c) sodium polyacrylate, hydrogenated polydecene and Trideceth; (d) propylene glycol, diazolidinyl urea, methylparaben and propylparaben; (d) ethoxydiglycol; (e) ginseng extract; (f) arnica extract; and (g) gingko biloba extract.

13. The composition for treating hot flashes of claim 1, wherein the composition is a topical gel.

14. A composition for treating hot flashes comprising:
    a) an ingredient effective to objectively lower skin temperature in combination with inactive ingredients so as to form a topical ointment effective to objectively actually lower skin temperature when applied to the skin, the effective ingredient comprising menthol and about 0.1 to less than about 1 percent of peppermint oil, wherein the composition comprises the menthol in an amount of about 0.1 to less than about 1 percent in addition to any menthol present in the present oil;

b) butylene glycol;
c) at least one of: (i) dimethicone; (ii) trisiloxane; (iii) Ceteth-10; or (iv) Laureth-4;
d) sodium polyacrylate, hydrogenated polydecene and Trideceth;
e) at least one of: (i) propylene glycol; (ii) diazolidinyl; urea; (iii) methylparaben; and (iv) propylparaben;
f) ethoxydiglycol;
g) ginseng extract;
h) arnica extract; and
i) gingko biloba extract.

15. The composition for treating hot flashes of claim 14, wherein the topical hot flash treatment composition is topical gel.

16. A composition for treating hot flashed comprising:
a) an ingredient effective to objectively lower skin temperature in combination with inactive ingredients so as to form a topical ointment effective to actually objectively lower skin temperature when applied to the skin, the effective ingredient comprising menthol and about 0.1 to less than about 1 percent of spearmint oil, wherein the composition comprises the menthol in an amount of about 0.1 to less than about 1 percent in addition to any menthol present in the spearmint oil;
b) glycol;
c) at least one of: (i) dimethicone; (ii) trisiloxane; (iii) Ceteth-10; or (iv) Laureth-4;
d) sodium polyacrylate, hydrogenated polydecene and Trideceth;
e) at least one of; (i) propylene glycol; (ii) diazolidinyl urea; (iii) methylparaben; and (iv) propylparaben;
f) ethoxydiglycol;
g) ginseng extract;
h) arnica extract; and
i) gingko biloba extract.

17. The composition for treating hot flashes of claim 16, wherein the topical hot flash treatment composition is a topical gel.

18. A topical composition for treating hot flashed comprising:
a) an amount of menthol in the composition combined with inactive ingredients so as to form a topical ointment capable of objectively lowering a skin temperature when applied to the skin to relieve a hot flash; and
b) wherein the composition comprises about 0.1 to less than about 1 percent of at least one of: (1) spearmint oil; or (2) peppermint oil, and wherein the composition comprises the menthol in the amount of about 0.1 to less than about 1 percent in addition to any menthol present in the at least one of the spearmint oil or peppermint oil; and
c) one or more extracts of: (1) ginsing; (2) arnica; or (3) gingko biloba.

19. The composition for treating hot flashes of claim 18, wherein the amount of menthol in the composition is such that is subjectively relieves a hot flash when topically applied as a hot flash remedy.

20. The composition for treating hot flashes of claim 18, wherein the topical hot flash treatment composition comprises the peppermint oil.

21. The composition for treating hot flashed of claim 18, wherein the topical hot flash treatment composition comprises the spearmint oil.

22. The composition for treatment hot flashes of claim 18, wherein the topical hot flash treatment composition is a topical gel.

* * * * *